US006762041B2

(12) United States Patent
Shimba et al.

(10) Patent No.: US 6,762,041 B2
(45) Date of Patent: Jul. 13, 2004

(54) METHOD FOR ISOTOPE LABELING OF PROTEIN WITH ENZYME

(75) Inventors: Nobuhisa Shimba, Kawasaki (JP); Eiichiro Suzuki, Kawasaki (JP); Keiichi Yokoyama, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 87 days.

(21) Appl. No.: 09/850,031

(22) Filed: May 8, 2001

(65) Prior Publication Data

US 2001/0044127 A1 Nov. 22, 2001

(30) Foreign Application Priority Data

May 15, 2000 (JP) ...................... 2000-141152

(51) Int. Cl.[7] .......................... C12P 13/14; C12N 9/10
(52) U.S. Cl. ................................ 435/128; 435/193
(58) Field of Search ............................... 435/128, 193

(56) References Cited

U.S. PATENT DOCUMENTS

| 4,582,794 A | * | 4/1986 | Russell ........................ 435/16 |
| 5,156,956 A | | 10/1992 | Motoki et al. |
| 5,658,605 A | * | 8/1997 | Soeda et al. .................... 426/7 |
| 5,817,474 A | | 10/1998 | Brown |
| 5,827,712 A | | 10/1998 | Yokoyama et al. |
| 5,846,998 A | * | 12/1998 | Schieven .................... 514/492 |
| 6,146,842 A | * | 11/2000 | Josiah et al. .................. 435/15 |

FOREIGN PATENT DOCUMENTS

DE   3834233   4/1990

OTHER PUBLICATIONS

Boyd et al., "The Influence of a Scaler–Coupled Deuterium Upon the Relaxation of a N15 Nucleus and its Possible Exploitation as a Probe of Side–Chain Interactions in Proteins" (1997) J. Biol. Chem., 124(1), 61–71.*

Signorini et al., "Identification of Transglutaminase Activity in the Leaves of Silver Beet (*Beta vulgaris* L.)" (1991) Journal of Plant Physiology, 137(5), 547–52, in Database CAPLUS, DN 114:244282.*
Takagi et al., "Modification of Transglutaminase Assay: Use of Ammonium Sulfate to Stop the Reaction" (1986) Analytical Biochemistry, 153(2), 295–8.*
Muszbek et al., "Kinetic Determination Of Blood Coagulation Factor–XIII In Plasma" (1985) Clin. Chem., 31(1), 35–40, in Database BIOSIS, DN BA79:64845.*
Dutton et al., "Crosslinking and Labeling of Membrane Proteins by Transglutaminase–Catalyzed Reactions" (1975) Proc. Nat. Acad. Sci. USA, 72(7), 2568–2571.*
V. Iwanij, "The Use of Liver Transglutaminase for Protein Labeling," Eur. J. Biochem., vol. 80, pp. 359–368 (1977).
D.S. Wilbur, "Radiohalogenation of Proteins: An Overview of Radionuclides, Labeling Methods, and Reagents for Conjugate Labeling," Bioconjugate Chemistry, vol. 3, No. 6, pp. 438–439 (1992).
M. Sattler, et al., "Use of Deuterium Labeling in NMR: Overcoming a Sizeable Problem," Structure, vol. 4, No. 11, pp. 1245–1249 (1996).
P.M. Nielsen, "Reactions and Potential Industrial Applications of Transglutaminase," Food Biotechnology, vol. 9(3), pp. 119–156 (1995).

* cited by examiner

Primary Examiner—Jon P. Weber
(74) Attorney, Agent, or Firm—Oblon, Spivak, McClelland, Maier & Neustadt, P.C.

(57) ABSTRACT

The present invention provides a method for isotopically labeling a functional group possessed by an amino acid residue of a protein. The present invention also provides a protein whose functional group in an amino acid residue is isotopically labeled.

A functional group in an amino acid residue of a protein is substituted with an isotope-labeling group derived from an isotope-labeling compound by making use of the action of an enzyme. In particular, the carboxyamide nitrogen atom in a glutamine residue of a protein is replaced with an isotopically labeled atom by acting a transglutaminase on the glutamine residue.

16 Claims, 7 Drawing Sheets

SCHEME FOR $^{15}$N-LABELING OF CARBOXAMIDE NITROGEN ATOM ON A GLUTAMINE RESIDUE

FIG. 1
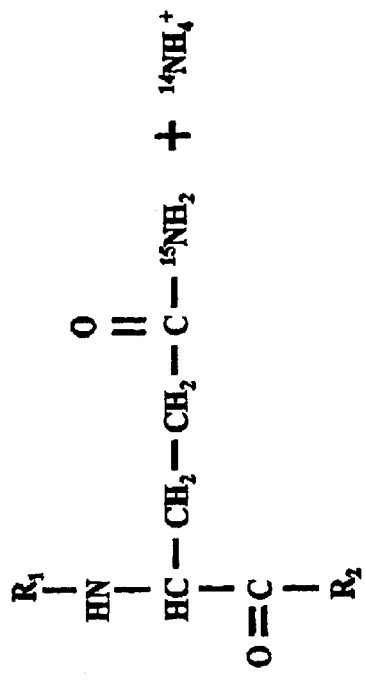
COMPOUNDS REPRESENTED BY FORMULA (1)
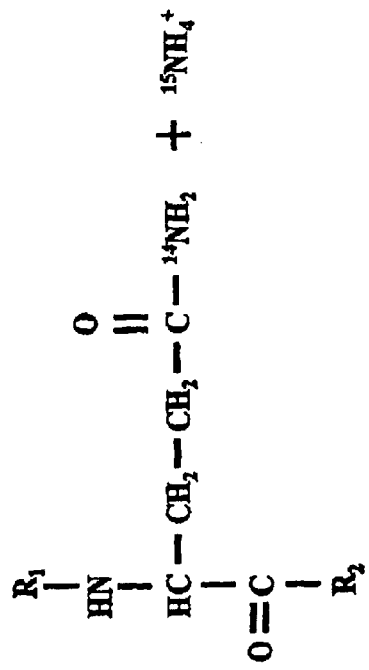
COMPOUNDS REPRESENTED BY FORMULA (2)
SCHEME FOR $^{15}$N-LABELING OF CARBOXAMIDE NITROGEN ATOM ON A GLUTAMINE RESIDUE CBZ-Gln-Gly
HSQC CBZ-Gln-Gly
$^1$H-NMR

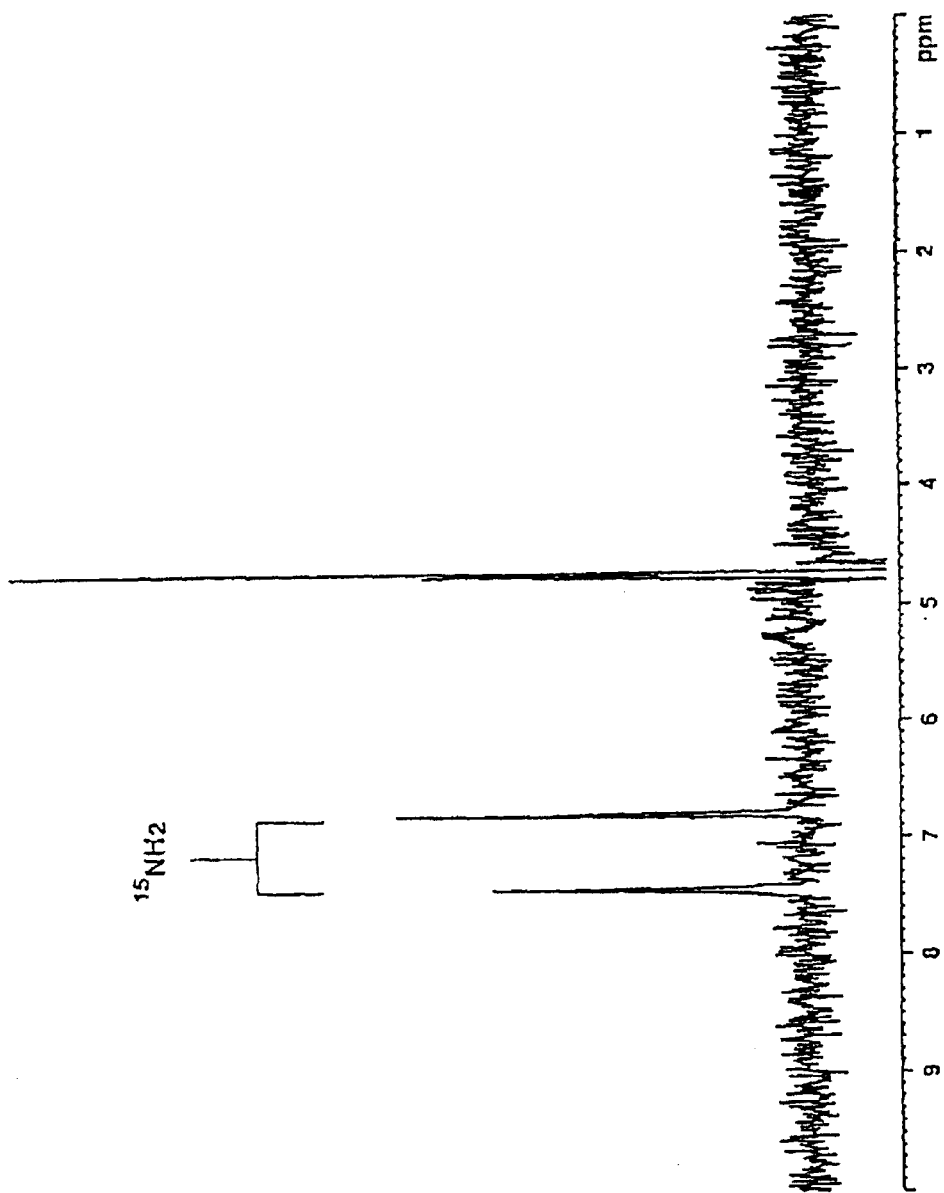

15N-LABELING BY TRANSGLUTAMINASE FROM GUINEA PIG

15N-LABELING BY MTG

METHOD FOR ISOTOPE LABELING OF PROTEIN WITH ENZYME

BACKGROUND OF THE INVENTION

The present invention relates to a method for isotopically labeling a functional group of an amino acid residue of a protein and a protein whose amino acid residues have an isotopically labeled functional group.

As the genome analysis technique has been advanced, the genes of a variety of animals, plants and microorganisms have been revealed one after another. Moreover, efforts have recently been put into the post-genome studies, for example the development of pharmaceuticals based on the gene information. In particular, the structure of a protein encoded by specific genes obtained and the functions thereof have extensively been analyzed in order to elucidate the roles of the genes. This is because, if it is found that such a protein is, for instance, a receptor protein, one can find out agonists or antagonists by screening the ligands therefor. However, there has not yet been known any standardized method for analyzing functions and structures of proteins unlike the gene sequence analysis and accordingly, and it is necessary to use or select an appropriate method depending on the purposes. Among these, a method for labeling a target protein has widely been used because the method makes the detection of the target protein easy.

As means for labeling protein, there may be listed, for instance, a method for incorporating isotopes such as $^2H$, $^{13}C$ and $^{15}N$ into the protein; and a method for chemically modifying the protein with a fluorescent reagent or a chelating agent. The development of proteins labeled with stable isotopes such as $^2H$, $^{13}C$ and $^{15}N$ can considerably extend the scope of NMR applications and the isotope-labeled proteins have widely been used as a means indispensable to the structural studies with NMR (see, for instance, Ikura, M. et al. Science, 1992, 256:632). In addition, such isotope-labeled proteins have frequently been used in the functional analysis while making the most use of the fact that they can be detected by several techniques such as NMR and MS. On the other hand, the chemical modification of a protein with a fluorescent reagent or a chelating agent is suited to the detection of trace samples and therefore, it has widely been used for determining the distribution of proteins and for quantitative analysis of the activity of the proteins.

As characteristic properties of the foregoing stable isotopes, there may be listed, for instance, any chemical property of a protein is not fundamentally changed through the labeling with such an isotope at all. Accordingly, stable isotopes have been put into practical use in the structural and functional analysis of proteins. In particular, in the structural analysis of proteins by means of the NMR technique, there have been known a method for reducing the number of signals of $^1H$ present in a protein by labeling the protein with $^2H$ to thus make the analysis thereof easy (a negative labeling method) and a method in which highly sensitive nuclides such as $^{13}C$ and $^{15}N$ are substituted for C and N, respectively, present in the protein to thus utilize the isotope-labeled protein in the multi-dimensional NMR technique (a positive labeling method). At the present time, most of proteins having a molecular weight of not less than 6000 have been subjected to structural analysis using either of these methods.

Labeling a protein with a stable isotope is mainly conducted by constructing an expression system of *E.coli* and then cultivating *E.coli* in a culture medium containing a labeling compound. In this respect, examples of such labeling compounds include $^{13}C$ glucose, $^{15}NH_4Cl$, $^{13}C$ glycerol and a variety of labeling amino acids (see, for instance, Kainosho, M. et al. Biochemistry, 1982, 21:6273; and Ikura, M. et al. Biochemistry, 1990, 29:4659). There has also been reported a method for preparing a labeled protein by the use of an expression system such as yeast or animal cells or cell-free systems, in addition to *E.coli* system (Kigawa, T. et al. J. Biomol. NMR, 1995, 2:129). In these methods, a labeling compound is incorporated therein during the biosynthesis of peptide chains. Therefore, a protein may site-directively or uniformly be labeled. However, it is necessary to construct an expression system for individual proteins and this requires a great deal of labor and time. In case of peptides and proteins having a short chain length, they may be synthesized using labeled amino acids, but this method is limited in objects to which the method is applied because of the restriction in the chain length.

On the other hand, the chemical modification permits the direct labeling of any protein prepared without any pre-treatment and there are not so many restrictions. Moreover, there have been known chemically modifying agents suited to individual functional group-carrying residue such as glutamic acid residue, aspartic acid residue and histidine residue, respectively, and therefore, any protein can be labeled irrespective of the composition of the peptide chain thereof. However, the chemical modification may, for instance, add a functional group having characteristic properties different from that of a natural protein. Accordingly, some of the functions and/or the structure of the natural protein may sometimes be damaged and there is a limit in the application of the chemical modification to the functional analysis and the structural analysis.

SUMMARY OF THE INVENTION

It is an object of the present invention to provide a method for isotopically labeling a functional group of an amino acid residue of a protein.

It is another object of the present invention to provide a protein whose amino acid residue has a functional group isotopically labeled.

The use of such a protein whose amino acid residue has a functional group isotopically labeled would permit the functional analysis and the structural analysis of the isotopically labeled protein.

The inventors of this invention have conducted various studies to solve the foregoing problems associated with the conventional techniques, have found that the functional group possessed by an amino acid residue of a protein can be labeled with an isotope while making use of the activity of an enzyme and have thus completed the present invention.

Accordingly, the present invention relates to a method for isotopically labeling a protein, which comprises the step of bringing the protein to be labeled, an isotope-labeling compound and an enzyme into contact with one another. More specifically, the present invention pertains to a method for isotopically labeling a protein, which comprises the step of bringing the protein to be labeled, an isotope-labeling compound and an enzyme into contact with one another to thus replace a desired functional group possessed by an amino acid residue of the protein with an isotope-labeling group derived from the foregoing isotope-labeling compound through the action of the enzyme.

In particular, the present invention relates to a method for isotopically labeling a protein, which comprises the step of acting a transglutaminase on the glutamine residue of a protein to label the carboxyamide nitrogen of the glutamine residue.

In addition, the present invention also embraces a protein isotopically labeled according to such a method.

BRIEF DESCRIPTION OF THE DRAWINGS

FIG. 1 represents a schematic diagram illustrating the process for $^{15}$N-labeling of carboxyamide nitrogen atom on a glutamine residue. In this figure, $R_1$ represents a peptide chain, an N-terminal amino acid residue or a hydrogen atom; and $R_2$ represents a peptide chain, a C-terminal amino acid residue or a hydroxyl group.

FIG. 3 represents a HSQC spectrum of $^{15}$N-labeled insulin B-chain.

DESCRIPTION OF THE PREFERRED EMBODIMENTS

Figure 2B:
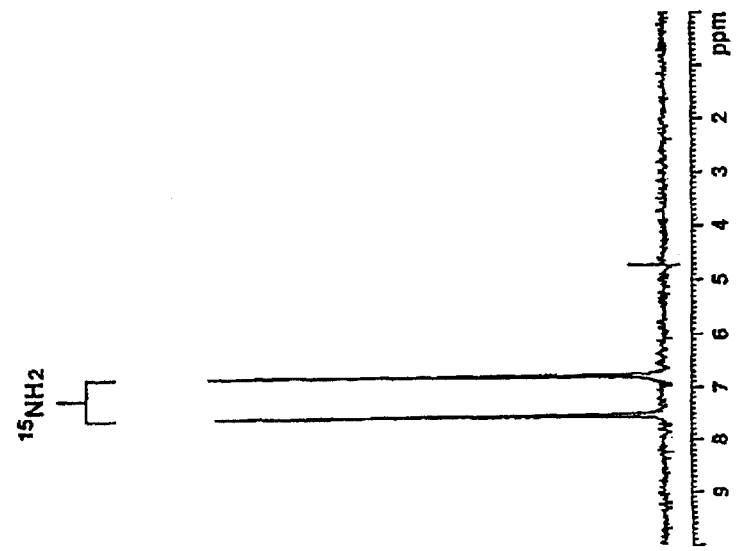
FIG. 2b represents a HSQC spectrum of $^{15}$N-labeled CBZ-Gln-Gly.

The enzyme used in the present invention may be any one inasmuch as it can act on a specific functional group of an amino acid residue of a protein to thus take part in the formation of a covalent bond therewith or the cleavage thereof. Preferred examples thereof include transferases, in particular, transglutaminase. In addition, it has been reported that methyl transferases also act on proteins and therefore, they may be used in the present invention (Clarke, S. et al. Proc. Natl. Acad. Sci. USA, 1988, 85:4643). Examples of such transferases also include hydroxy-transferases and amino-transferases in addition to the foregoing ones and they may likewise be used for the achievement of the objects of the present invention.

Transglutaminase is an enzyme widely used for a variety of industrial purposes. For instance, it has widely been used in, for instance, the production of foods such as gelatin, cheese, yoghurt, bean curd, boiled fish paste, ham, sausage and noodles and the quality-improvement of edible meat (Japanese Un-Examined Patent Publication No. 64-27471). Moreover, this enzyme has been used in the production of, for instance, materials for thermally stable microcapsules and carriers for immobilized enzymes. The transglutaminase catalyzes the acyl transfer reaction of the γ-carboxyamide of the glutamine residue present in the peptide chain of a protein molecule. In this respect, when the ε-amino group on a lysine residue in the protein molecule acts as an acyl-receptor, ε-(γ-Glu)-Lys bonds are created in the protein molecule and between the protein molecules.

FIG. 1 attached hereto schematically shows a method for isotopically labeling the carboxyamide nitrogen atom on the glutamine residue of a protein, using the catalytic reaction of the transglutaminase. Formulas (1) and (2) show two kinds of glutamine residue-containing proteins, respectively. In Formulas (1) and (2), $R_1$ represents a peptide chain, an N-terminal amino acid residue or a hydrogen atom; $R_2$ represents a peptide chain, a C-terminal amino acid residue or a hydroxyl group. These residues are not restricted to specific ones inasmuch as the protein may serve as a substrate for transglutaminase.

Transglutaminases are roughly divided into calcium-independent transglutaminase and calcium-dependent transglutaminase and both of them may be used in the present invention. Examples of the former include those derived from microorganisms such as Streptomyces and *Bacillus subtilis* (see, for instance, Japanese Un-Examined Patent Publication No. 64-27471). On the other hand, examples of the latter are those derived from the livers of guinea pigs (see, for instance, Japanese Examined Patent Publication No. 1-50382), human epidermal keratin cell transglutaminase (Phillips, M. A. et al. Proc. Natl. Acad. Sci. USA, 1990, 87:9333), human blood coagulation factor XIII (Ichinose, A. et al. Biochemistry, 1990, 25:6900), those derived from microorganisms such as Oomycetes, those derived from animals such as bovine blood and porcine blood, those derived from fishes such as salmons and red sea breams (see, for instance, SEKI Nobuo et al. "Bulletin of Japan Fisheries Society", 1990, 56:125–132), and those derived from oysters. In addition to the foregoing, examples of the calcium-dependent enzymes also include those prepared by the gene engineering (see, for instance, Japanese Un-Examined Patent Publication Nos. 1-300889, 6-225775 and 7-23737). Any transglutaminase may be used in the present invention irrespective of the origin and the production method of the enzyme.

In this respect, however, preferred are transglutaminases, which can act on a larger number of glutamine residues since the use of such a transglutaminase would permit the introduction of isotopic atoms into a large number of sites. In some cases, such an enzyme reaction in a solvent containing calcium is not preferred depending on the characteristic properties of proteins to be isotopically labeled. In such case or in case of such proteins, it is more preferred to use the foregoing calcium-independent transglutaminases. For instance, the transglutaminases derived from microorganisms (see, for instance, Japanese Un-Examined Patent Publication No. 64-27471) or the like may satisfy all of the foregoing requirements and they may presently be recognized to be optimum ones. Specific examples thereof are transglutaminases derived from microorganisms such as *Streptoverticillium griseocarneum* IFO 12776, *Streptoverticillium cinnamoneum* sub sp. Cinnamoneum IFO 12852 and *Streptoverticillium mobaraense* IFO 13819. The transglutaminase from *Streptoverticillium mobaraense* will hereafter be referred to as "MTG".

The unit of activity for the transglutaminases used in the present invention is determined and defined as follows. In other words, a reaction is carried out using benzyloxycarbonyl-L-glutaminyl glycine and hydroxylamine as substrates, followed by converting the resulting hydroxamic acid into an iron complex in the presence of trichloroacetic acid and determination of the amount thereof in terms of the absorbance thereof at a wavelength of 525 nm. Thus, a calibration curve is prepared on the basis of the amount of hydroxamic acid and the amount of the enzyme required for forming 1 μmol of hydroxamate per minute is defined to be the unit of activity of the enzyme, that is, one unit of the transglutaminase. The details of the determination method have already been reported (see, for instance, Japanese UnExamined Patent Publication No. 64-27471).

The proteins to be isotopically labeled according to the present invention may be a wide variety of proteins and specific examples thereof include human plasma components such as albumin, immunoglobulin and blood coagulation factors; enzymes such as proteases and transferases; hormones such as growth hormones and erythropoietin; cell proliferation factors involved in the cell proliferation and the inhibition of cell proliferation; immune reaction-regulatory factors involved in, for instance, the cell differentiation, induction and stimulation; and cell-producing biologically active proteins such as monokine, cytokine and lymphokine. Origins of these proteins are not restricted to specific ones and may be those derived from animals, plants and microorganisms. In addition, the proteins may be those from, for instance, $E.coli$, yeast and animal cells system, in which the genes coding for these proteins are integrated and expressed; or those expressed by using cell-free protein-synthesizing systems.

The molecular weight of the protein to be isotopically labeled is not restricted to any specific range, but it is preferably not more than $2 \times 10^5$ if it is detected by NMR. In cases where the molecular weight of the protein is not less than $2 \times 10^5$, the detection thereof by NMR becomes difficult because of broadening of the NMR signals and therefore, the detection thereof is performed by determination of mass spectra.

The proteins to be isotopically labeled with the transglutaminase are those containing at least one glutamine residue in the molecule, on which the transglutaminase acts. Whether the glutamine residue in the molecule is affected by the transglutaminase or not may be confirmed by determining the NMR or mass spectra of the isotopically labeled protein. For instance, if the carboxyamide nitrogen atoms of glutamine residues are labeled with $^{15}N$ by the activity of the transglutaminase, it is sufficient to determine the $^{15}N$ edited NMR spectra such as $^1H$-$^{15}N$ HSQC spectra. Alternatively, it is also possible to confirm the foregoing fact by detecting an increase in the molecular weight accompanied by the substitution of $^{14}N$ with $^{15}N$ according to the mass spectroscopy. Moreover, in case where a protein does not contain any glutamine residue affected by the transglutaminase, a glutamine residue affected by the transglutaminase can be introduced into the protein by the site-directed mutagenesis.

Examples of isotopes used for labeling proteins are $^2H$ or $^3H$ for $^1H$, $^{13}C$ for $^{12}C$, $^{15}N$ for $^{14}N$, and $^{17}O$ or $^{18}O$ for $^{16}O$. In case of naturally occurring proteins, they contain large number of $^1H$, $^{12}C$, $^{14}N$ and $^{16}O$ and therefore, these nuclides are frequently replaced with isotopes thereof. However, the present invention is not restricted to the isotope-labeling of hydrogen, carbon, nitrogen and/or oxygen atoms. Alternatively, it is also possible to prepare a protein containing nuclides existing at a low natural abundance ratio such as $^2H$, $^{13}C$ and $^{15}N$ and then isotopically label the resulting protein with nuclides existing at a high natural abundance ratio such as $^1H$, $^{12}C$ and $^{14}N$.

When the carboxyamide nitrogen atom of a glutamine residue of a protein is labeled with $^{15}N$ by the activity of the transglutaminase, the isotope is introduced into the protein through an exchange reaction with a labeled amine compound as shown in FIG. 1. It is sufficient to use an ammonium salt as the labeling compound and specific examples thereof include a wide variety of ammonium salts such as ammonium chloride and ammonium sulfate. More specifically, the nitrogen atom of the ammonium salt is $^{15}N$ for the labeling with $^{15}N$ or $^{14}N$ for the labeling with $^{14}N$.

The NMR, MS and neutron scattering techniques can recognize the isotopically labeled site. Among them, preferably used are NMR and MS techniques since they permit the rapid and easy analysis. In case of the NMR technique, there has been reported a method for editing for or filtering only specific isotope nuclei. Moreover, it has been known that individual atoms present in a protein are characterized by individual chemical shifts on the NMR spectra and therefore, they can be assigned to specific sites, respectively according to the existing method. For instance, the $^1H$-$^{15}N$ HSQC measurement corresponds to a method for editing only the $^{15}N$ nuclei and thus the method permits the confirmation of the introduction of $^{15}N$ nuclei. Moreover, it is also possible to specify the location of a specific isotopically labeled nitrogen atom on the protein molecule on the basis of the chemical shift of the $^{15}N$ nucleus observed on the $^1H$-$^{15}N$ HSQC spectrum.

In addition, the use of the MS technique permits the determination of the site isotopically labeled on a protein molecule. For instance, if proteins prior to or after the labeling with an isotope are subjected to partial cleavage using an enzyme, there has been observed a difference in the molecular weight between the peptide fragments containing the site which was isotopically labeled. The sequence of the peptide fragment can be determined by a method, which comprises the step of analyzing mass spectra or MS/MS while converting it into fragments for each residue and this accordingly permits the determination of the isotopically labeled site on the protein molecule. Moreover, if a protein has a molecular weight of not more than $2 \times 10^4$, the isotopically labeled site on the protein molecule can be determined by means of only the MS/MS technique without carrying out any partial cleavage of the protein with an enzyme.

Figure 2A:
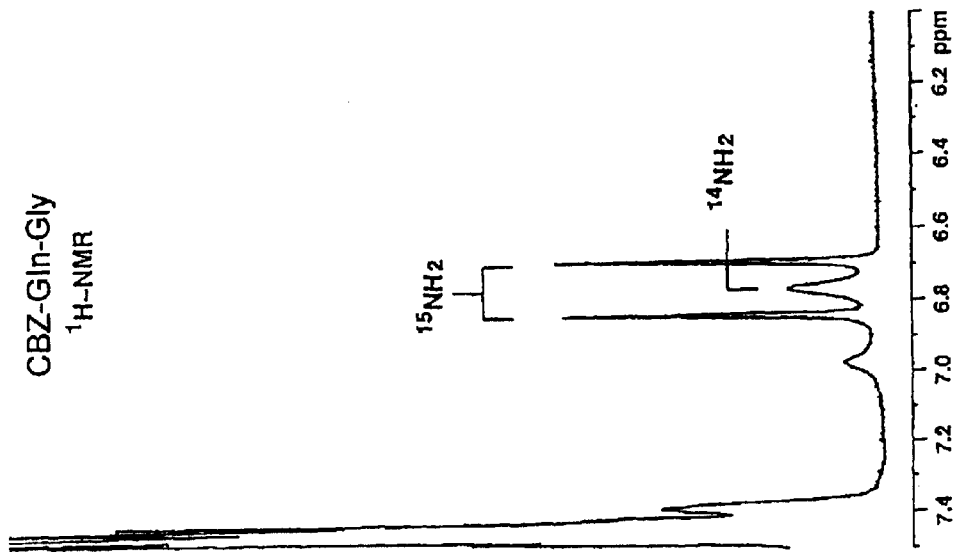
FIG. 2a represents a $^1$H NMR spectrum of $^{15}$N-labeled CBZ-Gln-Gly.

It is preferred to use the NMR technique as the method for quantitatively analyzing the rate of labeling. The intensity of the NMR signal and the abundance ratio are correlated with each other and accordingly, the rate of labeling can be calculated on the basis of the ratio of the signal intensity due to the isotopically labeled site to that due to the un-labeled site. For instance, if $^{15}N$ nuclei are introduced into carboxyamide groups, the labeled site corresponds to $^{15}N$-$^1H$, while the unlabeled site corresponds to $^{14}N$-$^1H$. At this stage, the $^{15}N$-$^1H$ is affected by the $^{15}N$ nucleus and therefore, the signal splits into doublet as will be seen from the data plotted on FIG. 2(a), but the signal for $^{14}N$-$^1H$ is observed as a singlet. As a result, the ratio of $^{15}N$-labeling can be estimated from each intensity ratio (see Examples as will be described later).

When analyzing the structure and/or functions of a protein or the substrate-specificity of transglutaminase, the rate of isotope-labeling is desirably not less than 90%. To label glutamine residues on which the transglutaminase acts at a labeling ratio of not less than 90%, it is sufficient to maintain the transglutaminase, a protein to be labeled and an isotope-labeling compound under the same conditions used in the usual transglutaminase reaction. For instance, a mixture of a protein to be labeled, an ammonium salt and a transglutaminase is maintained in an aqueous solvent, at a pH value ranging from about 5.0 to about 9.0, preferably about 6.0 to about 8.0 and at a temperature ranging from about 4° C. to about 55° C. and preferably about 25° C. to about 40° C. The reaction time is not particularly restricted, but it generally ranges from about 30 seconds to about 2 days and preferably about one minute to about 2 hours. In this reaction, the concentration of the protein to be labeled desirably ranges from about 1 $\mu$M to about 40 mM. On the other hand, the concentration of the ammonium salt desirably ranges from about 10 $\mu$M to about 10M and is not less than about 10 times and preferably not less than about 200 times the concentration of the protein to be labeled. Moreover, the amount of the transglutaminase to be used desirably ranges from about 10 nM to about 100 $\mu$M and this corresponds to about 0.01 to about 20 units per 1 mmol of the protein.

However, the present invention is not restricted to the foregoing reaction conditions and the labeling ratio may preferably be not more than 90% depending on the applications. For instance, this is applicable to the case wherein the activities of a variety of transglutaminases are evaluated by monitoring the isotope-labeling speed.

On the other hand, the substrate-specificities of the transglutaminases have conventionally been compared with one another while making use of a method, which comprises analyzing the crosslinked polymer obtained through a transglutaminase reaction by electrophoresis or a method, which comprises cleaving a reaction product into fragments and then analyzing the fragments. The former is suited to the monitoring of an intermolecular crosslinking reaction, but it is not suited for obtaining detailed information concerning the bonding sites and the number thereof. In addition, the latter method requires a great deal of labor and time and there is a limit in the application thereof to a variety of transglutaminases and a variety of substrate proteins.

Contrary to these conventional methods, the method according to the present invention permits the easy evaluation of the activities of a variety of transglutaminases including transglutaminase variants and the analysis of the substrate-specificity thereof and thus permits the screening of a specific transglutaminase suitably used in a specific application. To evaluate the activity of a transglutaminase and to analyze the substrate-specificity thereof, it is sufficient to react a transglutaminase with a substrate protein in the presence of a labeling agent under the foregoing reaction conditions and to detect glutamine residues in the substrate protein which are isotopically labeled, for instance, to monitor the change in the labeling ratio with time using NMR technique. As such NMR technique, there may be listed, for instance, an NMR technique which can selectively edit $^{15}$N nuclei such as $^{1}$H-$^{15}$N HSQC. Moreover, the method of the present invention may be used in a variety of applications by, for instance, observing any change in the reaction rate as a function of the pH value, the reaction temperature and/or the substrate concentration.

In addition, the substrate-specificity can be analyzed or the glutamine residues susceptible to the action of a transglutaminase and less susceptible to the action can be distinguished, while making use of the fact that the glutamine residue, on which a transglutaminase acts, can be specified by using the NMR or MS technique.

More specifically, the method of the present invention permits easy examination of the activities and substrate-specificities of the existing transglutaminases, novel transglutaminases and transglutaminase variants. Therefore, the method of the invention is industrially valuable and can be applied to, for instance, the screening of transglutaminases.

Incidentally, casein has been used for the quality improvement of edible meat by the use of a transglutaminase, as one of the substrates for the transglutaminase (Japanese Examined Patent Publication No. 1-50382). If a protein other than casein can improve the quality of meat, the fields of applications of the method can be expanded. Proteins, which may serve as a substrate for a transglutaminase, can be screened by the application of the method of the present invention to a variety of proteins and as a result, substrate proteins capable of being replaced with casein may be discovered. For instance, if a protein and an ammonium salt as a labeling agent are reacted with each other in the presence of a transglutaminase under the foregoing reaction conditions, only the protein capable of serving as a substrate for the transglutaminase is labeled with $^{15}$N. Accordingly, any protein capable of serving as a substrate for a specific transglutaminase can easily be distinguished through the use of the NMR technique.

The method of the present invention in which a protein is labeled with an isotope through the action of an enzyme can be applied to any protein and is advantageous in that the physical properties of the protein are not adversely affected by the labeling at all, unlike the chemical modification. Moreover, isotopically labeled proteins and the labeled sites thereof can be detected or identified by the isotope editing, the isotope filtration experiments with NMR or the molecular weight determination by the MS technique, and therefore, a technique for analyzing the functions or structures of proteins can be developed.

For instance, if the method of the present invention is carried out using a receptor protein in the presence or absence of a ligand, the ligand-binding site observed in the presence of the ligand is not labeled since it is covered with or blocked by the ligand. For this reason, if the ligand-binding site can be specified, one can design a ligand, which can more strongly be linked with the protein or the site. This would in turn result in the discovery of novel antagonists or agonists. It would be considered that the method of the invention can be applied not only to the studies of the receptor-ligand interactions, but also to the analysis of the protein-ligand interactions or protein-protein interactions.

Furthermore, the NMR signals from the protons linked to $^{14}$N atoms are often broadened because of the characteristics of $^{14}$N, as compared with signals from the protons linked to $^{15}$N. For this reason, the labeling with $^{15}$N would provide a great deal of information concerning the distances and thus this in turn leads to an increase of the structural information obtained by the NMR measurement. In addition, the protein includes a large number of protons in the molecule and therefore, the proton NMR signals are superposed and this makes the analysis thereof difficult. In such case, conveniently used herein are isotope-editing or isotope filtration experiments, which make use of an isotopically labeled sample. For instance, when the carboxyamide nitrogen atom possessed by the glutamine residue of a protein is labeled with $^{15}$N in the presence of a transglutaminase, the structural information of the glutamine residue can preferentially be extracted. In addition thereto, the method of the present invention can widely be applied to a variety of fields.

EXAMPLES

Example 1

$^{15}$N-Labeling of Model Compound and Quantitative Analysis of Ratio of $^{15}$N-Labeling In this Example, N-carbobenzoxy-L-glutaminyl-L-glycine (hereinafter referred to as "CBZ-Gln-Gly") was taken as a model compound to be isotopically labeled. There were mixed 37.5 mM of CBZ-Gln-Gly, 423 mM of $^{15}$NH$_4$Cl, and 40 $\mu$m of MTG, followed by $^{1}$H-NMR measurement and $^{1}$H-$^{15}$N HSQC measurement (see FIGS. 2a and 2b). The time elapsed after the preparation of the mixture was 18 minutes for the $^{1}$H-NMR measurement and 390 minutes for the $^{1}$H-$^{15}$N HSQC measurement and these elapsed times correspond to those required for the transglutaminase reaction. The glutamine residue labeled with $^{15}N$ gave two signals on the $^1H$-$^{15}N$ HSQC spectrum and therefore, this fact clearly indicated that the carboxyamide nitrogen of the glutamine residue was labeled with $^{15}N$ (see FIG. 2b). Moreover, there were observed $^{15}NH_2$ signals and singlet $^{14}NH_2$ signals (two groups each) splitted due to the presence of $^{15}N$, on the $^1H$-NMR spectrum. One group thereof is shown in FIG. 1a. Thus, the $^{15}N$-labeling rate could be calculated to be 67% based on the intensity ratio of the $^{15}NH_2$ signal to the $^{14}NH_2$ signal on the spectrum. The foregoing results clearly indicate that the carboxyamide nitrogen of the glutamine residue can be labeled with $^{15}N$ and that the labeling rate can be quantitatively analyzed. The use of the method, already reported, for the assignment of the NMR signals of proteins or the MS technique would permit the assignment of these NMR signals even if there are present a plurality of sites labeled with $^{15}N$. Accordingly, the method of the present invention permits the assignment of the sites labeled with $^{15}N$ through the use of a transglutaminase or the identification of the glutamine residue serving as a transglutaminase reaction site.

Example 2

$^5N$-Labeling of Low Molecular Weight Protein Carrying Only One Glutamine Residue There were admixed 0.5 mM of insulin B-chain, 401 mM of $^{15}NH_4Cl$ and 4 μm of MTG and the resulting mixture was subjected to $^1H$-$^5N$ HSQC measurement after 69 minutes from the preparation of the mixture (see FIG. 3). As a result, it was found that the carboxyamide nitrogen of one glutamine residue present in the insulin B-chain could be labeled with $^{15}N$. Thus, it was proved that a peptide or a low molecular weight protein could be labeled with $^{15}N$.

Example 3

Figure 4B:
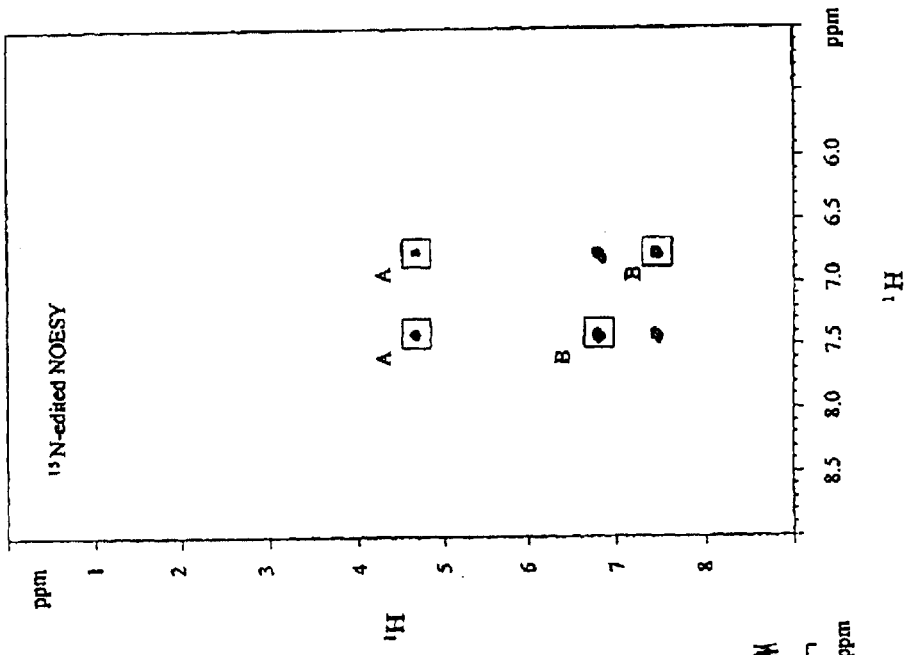
FIG. 4b represents a $^{15}$N-edited NOESY spectrum of $^{15}$N-labeled insulin A-chain.
Figure 4A:
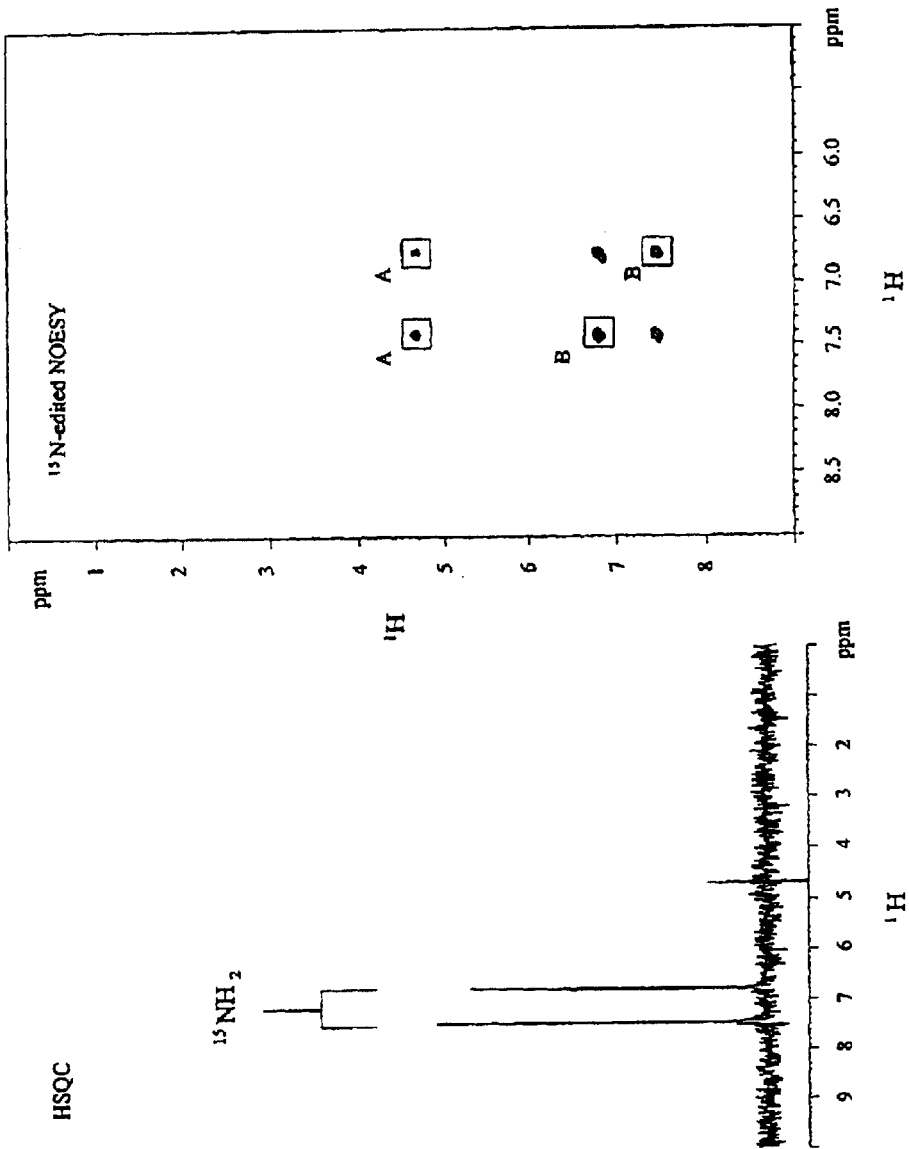
FIG. 4a represents a HSQC spectrum of $^{15}$N-labeled insulin A-chain.

$^{15}N$-Labeling of Low Molecular Weight Protein Carrying a Plurality of Glutamine Residues and Structural Analysis Thereof There were admixed 0.5 mM of insulin A-chain, 401 mM of $^{15}NH_4Cl$ and 4 μm of MTG and the resulting mixture was subjected to $^1H$-$^{15}N$ HSQC measurement after 20 minutes from the preparation of the mixture (see FIG. 4a). As a result, it was found that only the carboxyamide nitrogen of the two glutamine residues present in the insulin A-chain could be labeled with $^{15}N$. This clearly indicates that only the glutamine residue on which the transglutaminase acts is labeled with $^{15}N$.

Alternatively, the insulin A-chain whose carboxyamide nitrogen atom on the glutamine residue had been labeled with $^{15}N$ was subjected to $^{15}N$-edited NOESY measurement (see FIG. 4b). As a result, there were observed NOE or chemical exchange cross-peaks between protons of the carboxyamide group on the glutamine residue (FIG. 4b-B) or between the proton and a water molecule (FIG. 4b-A). NOE is a phenomenon observed between the protons present within a distance of about 0.5 nm and the chemical exchange means that a specific atom is exchanged between different states, for instance, between an amide proton and a proton of a water molecule. More specifically, it was confirmed that the distance between the carboxyamide protons of the glutamine residue is short (FIG. 4b-B) and that they are exposed to water molecules (FIG. 4b-A). From the foregoing results, it was found that information concerning the three-dimensional structure of a protein can be obtained by labeling the carboxyamide nitrogen of the glutamine residue with $^{15}N$.

Example 4

$^{15}N$-Labeling of High Molecular Weight Protein

Figure 5:
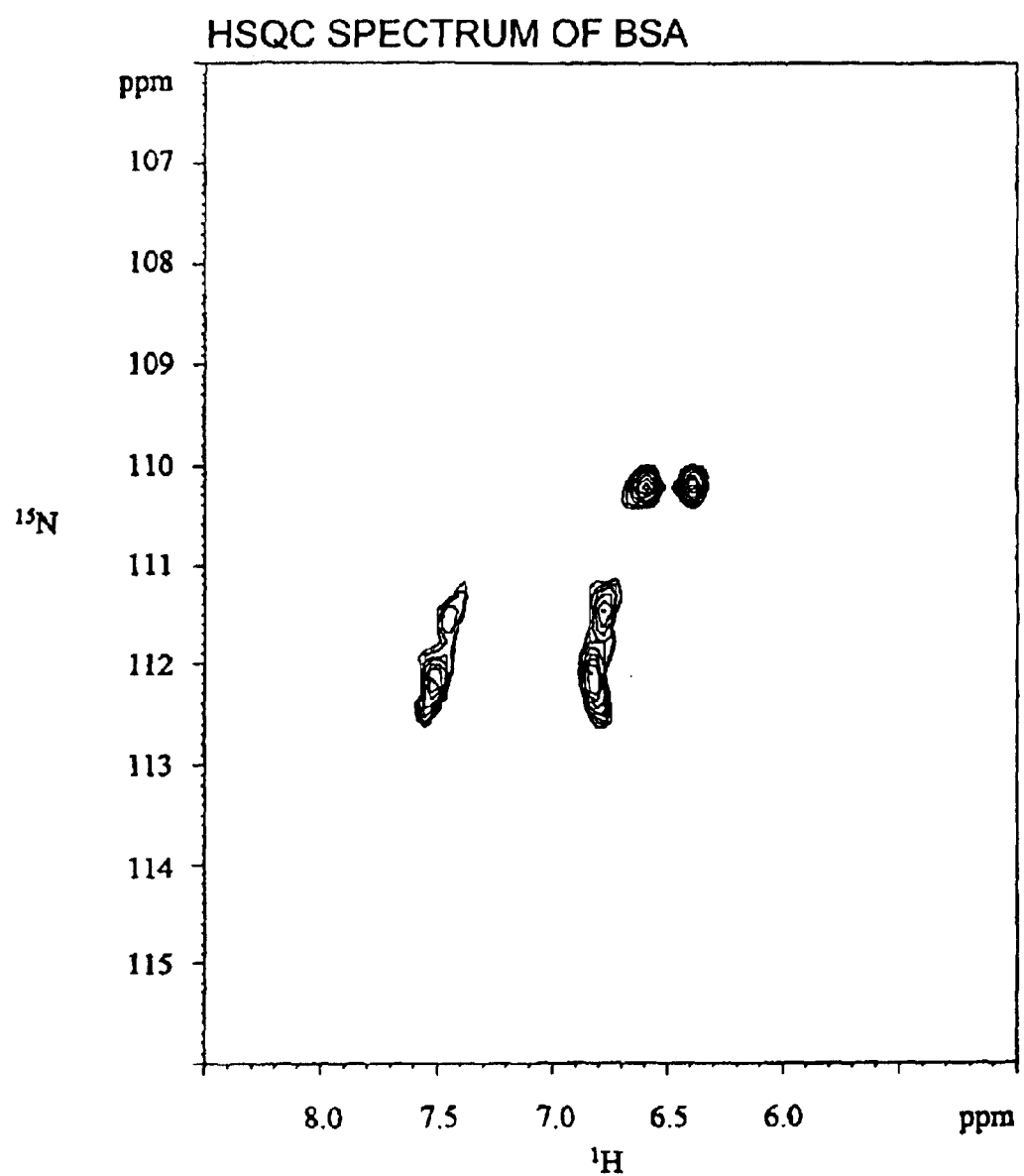
FIG. 5 represents a HSQC spectrum of $^{15}$N-labeled bovine serum albumin.

In this Example, bovine serum albumin (hereafter referred to as "BSA") was used as a high molecular weight protein. There were admixed 0.8 mM of BSA, 317 mM of $^{15}NH_4Cl$ and 4 μM of MTG, followed by subjecting the resulting mixture to $^1H$-$^{15}N$ HSQC measurement after 222 minutes from the preparation of the mixture (FIG. 5). If the carboxyamide nitrogen atom is labeled with $^{15}N$, there are observed two signals as a pair for the chemical shift ascribed to one $^{15}N$ atom since two $^1H$ atoms are bonded to the $^{15}N$ atom. As will be seen from the data shown in FIG. 5, at least part of the carboxyamide nitrogen atoms on the 21 glutamine residues present in the BSA molecule are labeled with $^{15}N$ and this clearly indicates that any high molecular weight protein can be labeled with $^{15}N$. Moreover, only the glutamine residues serving as sites for the transglutaminase reaction could be labeled with $^{15}N$ and as a result, it was found that the use of a protein containing a plurality of glutamine residues such as BSA would permit the comparison of substrate-specificities of various kinds of transglutaminases with one another.

Example 5

Protein Free of any Glutamine Residue on which Transglutaminase Acts

A mixture comprising 1.4 mM of egg white lysozyme, 415 mM of $^{15}NH_4Cl$ and 4 μm of MTG was prepared and then the resulting mixture was subjected to $^1H$–$^{15}N$ HSQC measurement after 722 minutes from the preparation of the mixture. As a result, it was found that all of the three glutamine residues present in the egg white lysozyme were not labeled with $^{15}N$ and that the egg white lysozyme did not serve as a substrate for a transglutaminase. Accordingly, it can be concluded that any substrate protein for the transglutaminase may easily be selected by trying to isotopically label a plurality of proteins using a transglutaminase.

Example 6

Comparison of Substrate-Specificities of Various Kinds of Transglutaminases with Each Other There are known various kinds of transglutaminases whose molecular weights and/or amino acid sequences are different from one another. The kinds of glutamine residues serving as substrates and the reaction rates vary depending on the kinds of the transglutaminases and this results in the difference in the ability of crosslinking substrate proteins. Under such circumstances, the substrate specificities were simply and rapidly compared with one another using the method according to the present invention.

Figure 6B:
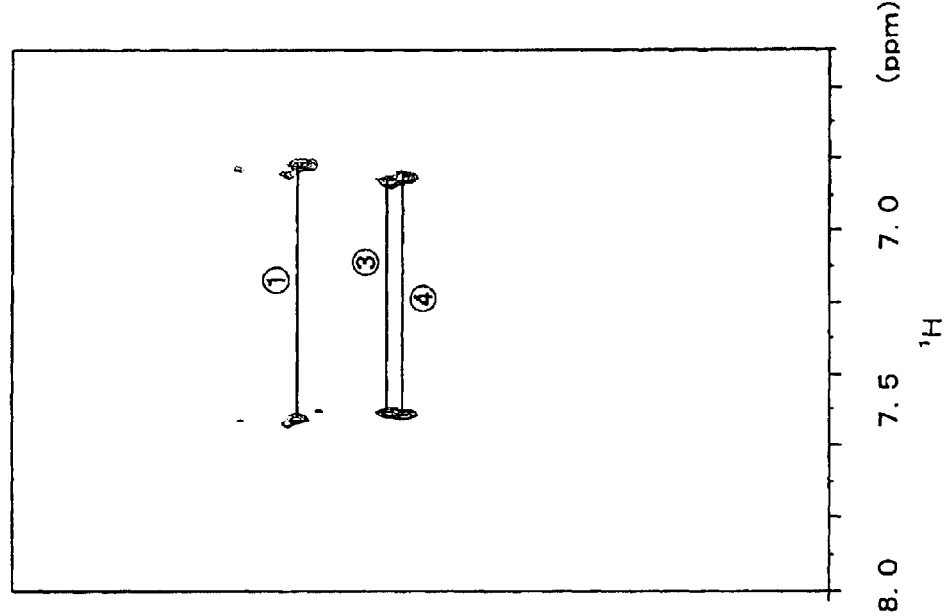
FIG. 6b represents a HSQC spectrum of ovalbumin labeled with $^{15}$N in the presence of the transglutaminase from Guinea pig.
Figure 6A:
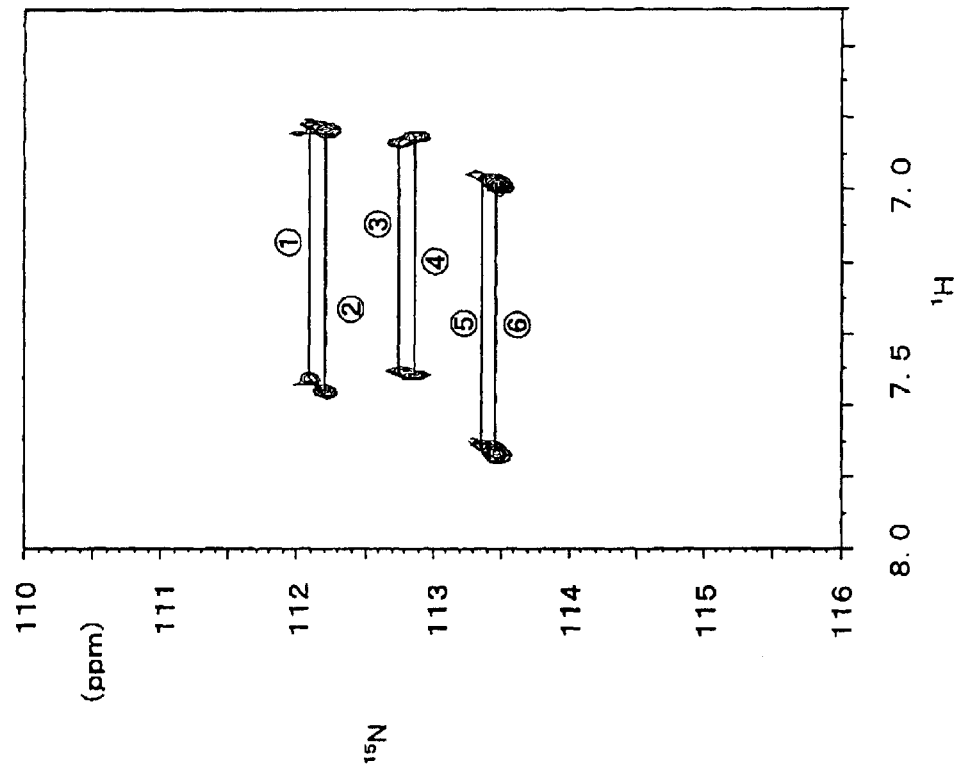
FIG. 6a represents a HSQC spectrum of ovalbumin labeled with $^{15}$N in the presence of MTG.

A mixture containing 2.3 mM of ovalbumin, 5 mM of $CaCl_2$, 200 mM of $^{15}NH_4Cl$ and 4 μM of MTG was prepared and the resulting mixture was subjected to $^1H$-$^{15}N$ HSQC measurement after 180 minutes from the preparation of the mixture (FIG. 6a). Similarly, they were reacted under the same conditions used above except that the transglutaminase derived from guinea pigs was purchased from Sigma Company and that the kind of the transglutaminase was changed and then the reaction product was subjected to $^1H$-$^5N$ HSQC measurement (FIG. 6b). As a result, it was found that among the glutamine residues 1 to 6 capable of being isotopically labeled using MTG, only the glutamine residues 1, 3 and 4 were labeled, in case where the labeling was performed in the presence of the transglutaminase from guinea pigs. It could easily and rapidly be proved that when using ovalbumin as a substrate protein, a plurality of glutamine residues may serve as substrates for MTG as compared with the transglutaminase from guinea pigs or the former has a low substrate specificity as compared with the latter. The foregoing results indicate that the method of the present invention permits the selection or screening of a specific transglutaminase suitable for any specific application, for instance, a transglutaminase reacting with a larger number of glutamine residues or a transglutaminase reacting with a smaller number of glutamine residues.

Example 7

Comparison of Reaction Rates of any Glutamine Residue Present on Substrate Protein with Each other In this Example, reaction rates will be compared with one another subsequent to Example 6. As examples of MTG, there has been reported a variant thereof whose N-terminal aspartic acid residue is deleted (Japanese Un-Examined Patent Publication No. 11-075876). Therefore, the method of the present invention was applied to the mutant and a wild type of MTG. The variant whose N-terminal aspartic acid residue is deleted has a serine residue as the N-terminal and thus will hereafter be referred to as "Ser type".

Figure 7:
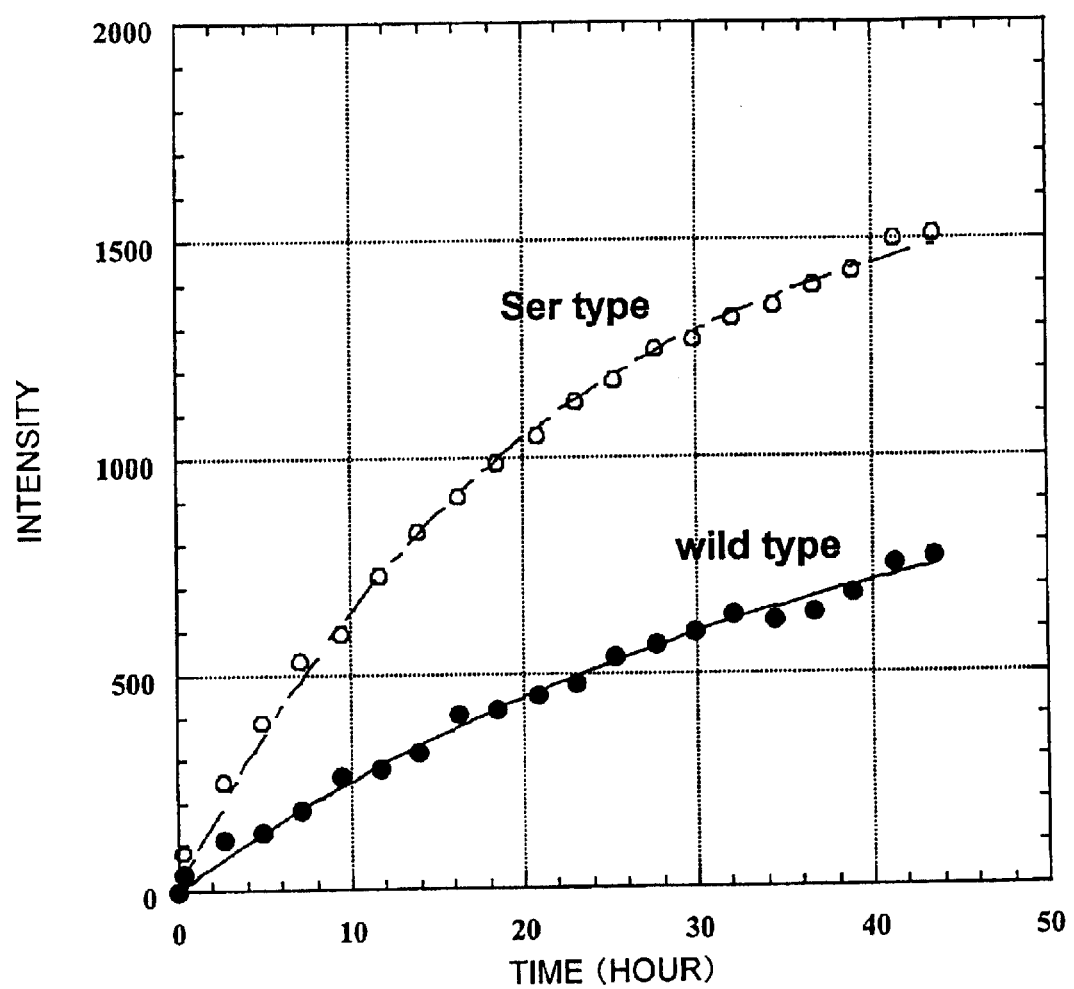
FIG. 7 represents a diagram on which the peak intensities of signals indicated by 6 in FIG. 6a, among the glutamine residues of ovalbumin on which the wild type or Ser type transglutaminase acts in the presence of $^{15}$NH$_4$Cl, are plotted as a function of the reaction time.

There was prepared a mixture of 2.3 mM of ovalbumin, 5 mM of $CaCl_2$, 200 mM of $^{15}NH_4Cl$ and 0.4 $\mu$M of the wild type MTG or Ser type and the resulting mixture was subjected to $^1H$-$^{15}N$ HSQC measurement continuously 20 times starting from 20 minutes after the preparation of the mixture in intervals of 136 minutes. Regarding the resulting spectra, the intensities of the signals indicated by 6 in FIG. 6(a) are plotted (FIG. 7). As a result, it was found that the reaction rate for the Ser type was higher than that observed for the wild type MTG at the site corresponding to the glutamine residue generating the signals indicated as 6 in FIG. 6(a). Thus, it can be proved that the method of the present invention permits the monitoring of the reaction rate of any glutamine residue present in a substrate protein. More specifically, it was found that the method of the present invention permits the simple and rapid screening of a variety of transglutaminases suited for specific applications such as a transglutaminase having a higher reaction rate or one having a lower reaction rate.

According to the present invention, any protein can be labeled with an isotope and this in turn makes the functional or structural analysis of such a protein easy. In particular, proteins carrying glutamine residues can be isotopically labeled by the action of transglutaminases. Moreover, the present invention can likewise be applied to the activity-evaluation of a variety of enzymes represented by transglutaminases and the comparison of substrate-specificities of such enzymes with each other as well as the determination of substrates.

It is also understood that the examples and embodiments described herein are only for illustrative purpose, and that various modifications will be suggested to those skilled in the art without departing from the spirit and the scope of the invention as hereinafter claimed.

What is claimed is:

1. A method for isotopically labeling a functional group possessed by an amino acid residue of a protein, comprising the step of reacting a transglutaminase with said protein in the presence of an isotope-labeled ammonium salt.

2. The method of claim 1, wherein said amino acid residue is a glutamine residue and said functional group is a γ-carboxamido group.

3. The method of claim 1, wherein said transglutaminase is calcium-independent.

4. The method of claim 1, wherein said transglutaminase is calcium-dependent and said reacting said transglutaminase with said protein is conducted in the presence of calcium.

5. The method of claim 1, wherein said transglutaminase is reacted with said protein in an aqueous environment at a pH of about pH5.0 to pH9.0 and a temperature of 4° C. to 55° C. for a time of about 30 seconds to about 2 days.

6. The method of claim 1, wherein the ratio of the concentration of said ammonium salt to the concentration of said protein to be labeled is more than about 10.

7. The method of claim 6, wherein the concentration of said protein to be labeled is about 1 $\mu$M to about 40 mM and the concentration of said ammonium salt is about 10 $\mu$M to about 10M.

8. An isotopically labeled protein, prepared by a process, comprising reacting a transglutaminase with a protein in the presence of an isotope-labeled ammonium salt, wherein said protein contains at least one glutamine residue on which said transglutaminase does not act and at least one glutamine residue on which said transglutaminase does act.

9. The isotopically labeled protein of claim 8, wherein said transglutaminase is reacted with a functional group of an amino acid residue and said amino acid residue is a glutamine residue and said functional group is a γ-carboxamido group.

10. The isotopically labeled protein of claim 8, wherein said transglutaminase is calcium-independent.

11. The isotopically labeled protein of claim 8, wherein said transglutaminase is calcium-dependent and said reacting said transglutaminase with said protein is conducted in the presence of calcium.

12. The isotopically labeled protein of claim 8, wherein said transglutaminase is reacted with said protein in an aqueous environment at a pH of about pH5.0 to pH9.0 and a temperature of 4° C. to 55° C. for a time of about 30 seconds to about 2 days.

13. The isotopically labeled protein of claim 8, wherein the ratio of the concentration of said ammonium salt to the concentration of said protein to be labeled is more than about 10.

14. The isotopically labeled protein of claim 13, wherein the concentration of said protein to be labeled is about 1 $\mu$M to about 40 mM and the concentration of said ammonium salt is about 10 $\mu$M to about 10M.

15. The isotopically labeled protein of claim 8, wherein said glutamine residue on which said transglutaminase acts is introduced into the protein by site-directed mutagenesis.

16. The isotopically labeled protein of claim 8, wherein said transglutaminase acts under a condition in which the three-dimensional structure of said protein is retained.

* * * * *